United States Patent
Huang et al.

(10) Patent No.: US 8,895,700 B2
(45) Date of Patent: Nov. 25, 2014

(54) MONKEY HOMOLOG OF HUMAN INTERFERON OMEGA

(75) Inventors: Chichi Huang, Radnor, PA (US); Jarrat Jordan, Radnor, PA (US); Jessica Schreiter, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 13/578,104

(22) PCT Filed: Feb. 16, 2011

(86) PCT No.: PCT/US2011/025052
§ 371 (c)(1),
(2), (4) Date: Aug. 9, 2012

(87) PCT Pub. No.: WO2011/103164
PCT Pub. Date: Aug. 25, 2011

(65) Prior Publication Data
US 2012/0308482 A1    Dec. 6, 2012

Related U.S. Application Data

(60) Provisional application No. 61/305,702, filed on Feb. 18, 2010.

(51) Int. Cl.
| | | |
|---|---|---|
| C07K 14/52 | (2006.01) | |
| C07K 14/00 | (2006.01) | |
| C07K 14/555 | (2006.01) | |
| G01N 33/68 | (2006.01) | |
| A61K 38/19 | (2006.01) | |
| A61K 38/21 | (2006.01) | |

(52) U.S. Cl.
CPC .......... *C07K 14/555* (2013.01); *G01N 33/6866* (2013.01)
USPC .......... 530/351; 530/350; 424/85.1; 424/85.4

(58) Field of Classification Search
None
See application file for complete search history.

(56) References Cited

U.S. PATENT DOCUMENTS

| | | | |
|---|---|---|---|
| 5,116,964 A | 5/1992 | Capon et al. | |
| 5,317,089 A | 5/1994 | Adolf | |
| 5,709,859 A | 1/1998 | Aruffo et al. | |
| 6,018,026 A | 1/2000 | Sledziewski et al. | |
| 7,597,884 B2 * | 10/2009 | Blatt et al. | 424/85.4 |
| 2002/0025304 A1 | 2/2002 | Croze et al. | |
| 2008/0019943 A1 | 1/2008 | Carter et al. | |
| 2009/0053173 A1 | 2/2009 | Fu et al. | |

FOREIGN PATENT DOCUMENTS

| | | |
|---|---|---|
| WO | WO 2004/002417 A2 | 1/2004 |
| WO | WO 2004/002424 A2 | 1/2004 |
| WO | WO 2005/032460 A2 | 4/2005 |
| WO | WO 2005/081687 A2 | 9/2005 |

OTHER PUBLICATIONS

Adolf, et al., "Purficiation and characterizaton of natural human interferon omega I. Two alternative cleavage sites for the signal peptidase," Journal of Biological Chemistry, 265: 9290-9295 (1990).
Bird, et al., "Single-Chain Antigen-Binding Proteins," Science, 242: 423-426 (1988).
Cutrone, et al., "Protein Structure and Folder: Identification of Critical Residues in Bovine IFNAR-1 Responsible for Interferon Binding," Journal of Biological Chemistry, 276: 17140-17148 (2001).
GenBank Accession No. CT573219, Priority Date: Jul. 12, 2006.
GenBank Accession No. NP_002168, Priority Date: Dec. 23, 2012.
GenBank Accession No. X58822, Priority Date: Apr. 18, 2005.
GenBank Accession No. XM_528554 Date: Oct. 25, 2012.
GenBank Accession No. XM_001108113, Priority Date: Jun. 1, 2010.
Gentz, et al. "Bioassay for trans-activation using purified human immunodeficiency virus *tat*-encoded protein: Trans-activation required mRNA synthesis," Proceedings of the National Academy of Science USA, 86: 821-824 (1989).
Hardy, et al., "The soluble murine type I interferon receptor Ifnar-2 is present in serum, is independently regulated, and has both agonistic and antagonistic properties," Blood, 97: 473-482 (2001).
Huston, et al., Protein engineering of antibody binding sites: Recovery of specific activity in an anti-digoxin single-chain Fv analogue produced in *Escherichia coli*, "Proceedings of the National Academy of Science, USA, " 85: 5879-5883 (1988).
Loisel, et al., "Relevance, adavantages and limitations of animal models used in the development of monoclonal antibodies for cancer treatment," Critical Reviews in Oncology/Hematology, 62: 34-42 (2007).
Ward, et al., "Binding activities of repertoire of single immunoglobulin variable domains secreted from *Escherichia coli,*"Nature, 341: 544-546 (1989).
Wilson, et al., "The Structure of an Antigenic Determinant in a Protein," Cell, 37: 767-778 (1984).
PCT International Search Report dated Apr. 29, 2011.
Supplementary European Search Report dated Oct. 10, 2013.

(Continued)

*Primary Examiner* — Christine J Saoud
*Assistant Examiner* — Jegatheesan Seharaseyon
(74) *Attorney, Agent, or Firm* — Eric Dichter (57) ABSTRACT

Cytokine IFNω nucleic acids from the Cynomolgus monkey are useful for expression of IFNω proteins that are functional homologs of human IFNω. The nucleic acids and proteins produced therefrom are useful in screening and safety testing of IFNω, the generation and testing of IFNω modulators and related activities.

2 Claims, 3 Drawing Sheets

(56) References Cited

OTHER PUBLICATIONS

Buckwold et al., "Safety Pharmacology, Toxicology and Pharmacokinetic Assessment of Recombinant Human Interferon Produced from CHO-SS Cells," Basic & Clinical Pharmacology & Toxicology, 99; 62-70 (2006).

Osada et al., "Assignment of 118 novel cDNAs of eynomologus monkey brain to human chromosomes," Gene, 275, 31-37 (2001).

Tanaka, et al., "ERas Is Expressed in Primate Embryonic Stem Cells But Not Related to Tumorigenesis," Cell Transplantation, 18: 381-389 (2009).

GenBank Accession Number AW137366, Established Date Jan. 6, 2011.

GenBank Accession Number AW137338, Established Date Jan. 6. 2011.

* cited by examiner

SEQUENCE LISTING

<160> NUMBER OF SEQ ID NOS: 8

<210> SEQ ID NO 1
<211> LENGTH: 603
<212> TYPE: DNA
<213> ORGANISM: Cynomolgus monkey

<400> SEQUENCE: 1

```
atggccctcc tcttccctct gctggcagcc ctagtgatga ccagctatag tcctgttgga      60
tctctgggct gtgatctgcc tcagaaccat ggcctactta gcaggaacac cttggtgctt     120
ctgcaccaaa tgaggagaat ctcccctttc ttgtgtctca aggacagaag agacttcagg     180
ttcccccagg agatggtaga agggagccag ctgcagaagg cccaggtcat gtctgtcctc     240
catgagatgc tacagcagat cttcagcctc ttccacacag agcactcctc tgctgcctgg     300
aacacgaccc tcctagacca tctccacact ggacttcacc ggcaactaga acacctggag     360
acctgcttgg tgcaggtaat gcgagaagga gaatctgctg gggcgattag gagccctgca     420
ctgaccttga ggaggtactt ccagggaatc cgtgtctacc tgaaagagaa gaaatacagc     480
gactgtgcct gggaagttgt cagaatggaa atcatgaaat ccttgttctt atcaacaaac     540
atgcaagaaa gactgaaaag taaagatgga gacctggggt catcttgaaa tgattctcat     600
tga                                                                   603
```

<210> SEQ ID NO 2
<211> LENGTH: 195
<212> TYPE: PRT
<213> ORGANISM: Cynomolgus monkey

<400> SEQUENCE: 2

```
Met Ala Leu Leu Phe Pro Leu Leu Ala Ala Leu Val Met Thr Ser Tyr
 1               5                  10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Glu Gly Ser Gln Leu Gln Lys Ala Gln Val Met Ser Val Leu
65                  70                  75                  80

His Glu Met Leu Gln Gln Ile Phe Ser Leu Phe His Thr Glu His Ser
                85                  90                  95

Ser Ala Ala Trp Asn Thr Thr Leu Leu Asp His Leu His Thr Gly Leu
            100                 105                 110
```

His Arg Gln Leu Glu His Leu Glu Thr Cys Leu Val Gln Val Met Arg
            115                 120                 125

Glu Gly Glu Ser Ala Gly Ala Ile Arg Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Lys Ser Lys Asp Gly Asp Leu
                180                 185                 190

Gly Ser Ser
        195

<210> SEQ ID NO 3
<211> LENGTH: 195
<212> TYPE: PRT
<213> ORGANISM: Homo sapiens

<400> SEQUENCE: 3

Met Ala Leu Leu Phe Pro Leu Leu Ala Ala Leu Val Met Thr Ser Tyr
1               5                   10                  15

Ser Pro Val Gly Ser Leu Gly Cys Asp Leu Pro Gln Asn His Gly Leu
            20                  25                  30

Leu Ser Arg Asn Thr Leu Val Leu His Gln Met Arg Arg Ile Ser
            35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
            115                 120                 125

Glu Gly Glu Ser Ala Gly Ala Ile Ser Ser Pro Ala Leu Thr Leu Arg
    130                 135                 140

Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
                180                 185                 190

Gly Ser Ser
        195

<210> SEQ ID NO 4
<211> LENGTH: 26
<212> TYPE: DNA
<213> ORGANISM: Artificial Sequence
<220> FEATURE:
<223> OTHER INFORMATION: Primer to clone cyno IFNw

<400> SEQUENCE: 4
atgtcttcag aaaacctagg gtccaa                                          26

```
<210> SEQ ID NO 5
<211> LENGTH: 23
<212> TYPE: DNA
<213> ORGANISM: Artificial Sequence
<220> FEATURE:
<223> OTHER INFORMATION: Primer to clone cyno IFNw

<400> SEQUENCE: 5
tgaccagagt cacatgtgca agt                                          23

<210> SEQ ID NO 6
<211> LENGTH: 48
<212> TYPE: DNA
<213> ORGANISM: Artificial Sequence
<220> FEATURE:
<223> OTHER INFORMATION: Primer to clone cyno IFNw

<400> SEQUENCE: 6
gctgggtacc agctgctagc gccaccatgg ccctcctctt ccctctgc               48

<210> SEQ ID NO 7
<211> LENGTH: 55
<212> TYPE: DNA
<213> ORGANISM: Artificial Sequence
<220> FEATURE:
<223> OTHER INFORMATION: Primer to clone cyno IFNw

<400> SEQUENCE: 7
tctgtttaaa cgggccctca atggtgatgg tgatgatgag atgacccag gtctc        55

<210> SEQ ID NO 8
<211> LENGTH: 19
<212> TYPE: DNA
<213> ORGANISM: Artificial Sequence
<220> FEATURE:
<223> OTHER INFORMATION: Primer to sequence cyno IFNw

<400> SEQUENCE: 8
ccaccagaca taatagctg                                               19
```

MONKEY HOMOLOG OF HUMAN INTERFERON OMEGA

CROSS REFERENCE TO RELATED APPLICATIONS

This application is a national stage of international Application Number PCT/US2011/025052, filed 16 Feb. 2011, which claims the benefit of U.S. Provisional Application No. 61/305,702, filed 18 Feb. 2010. The entire contents of each of the aforementioned application is incorporated herein by reference in its entirety.

FIELD OF THE INVENTION

The present invention relates to interferon omega, more particularly to a cynomolgus monkey homolog of human interferon omega and its uses.

BACKGROUND OF THE INVENTION

Type I interferons (IFN) (IFNα, IFNβ, IFNω, IFNκ, IFNε) are a family of structurally related cytokines having antiviral, antitumor and immunomodulatory effects (Hardy et al. Blood 97:473, 2001; Cutrone and Langer J. Biol. Chem. 276:17140, 2001. Type I interferon (IFN) is elevated in several inflammatory diseases and blockade of interferon alpha (IFNα) in particular holds promise in the treatment of a variety of autoimmune diseases, such as human systemic lupus erythematosus (SLE), or Primary Sjogren's Syndrome.

To elaborate on the therapeutic impact of using anti-human IFNω antibodies as well as to assess safety of the potential therapeutics in vivo, functional translational models are implemented through the use of non-human primate systems. Cynomolgus monkeys (*Macaca fascicularis*) are routinely used for pharmacokinetic and toxicological assessment of human biotherapeutics and the discovery of the orthologous IFNω sequence in the cynomolgus monkey would make it possible to develop in vitro assays needed to determine if cynomolgus IFNω exhibits sufficient structural and functional homology to human IFNω. A need in the art exists to improve current toxicological testing strategies through testing of closely related animal species with human or surrogate biologic proteins.

SUMMARY OF THE INVENTION

The invention provides *Macaca fascicularis* polynucleotides and polypeptides. One aspect of the invention is an isolated polynucleotide comprising a polynucleotide having the sequence shown in SEQ ID NO: 1 or a complementary sequence, fragment or variant thereof Another aspect of the invention is an isolated polypeptide comprising a polypeptide having the amino acid sequence shown in SEQ ID NO: 2 or a fragment or variant thereof In one aspect, the fragment is a polypeptide comprising residues 24-201 of SEQ ID NO: 2. In another aspect, the fragment is a polypeptide comprising residues 24-195 of SEQ ID NO: 2.

In another embodiment, the invention includes vectors and host cells comprising the polynucleotide having the sequence shown in SEQ ID NO: 1, the sequence encoding the amino acid sequence shown in SEQ ID NO: 2, or a complementary sequence, fragment or variant thereof In another embodiment, the polynucleotides of SEQ ID NO: 4, 5, and 6 are used to identify and isolate polynucleotides encoding IFNω homologs from cells, tissues, or fluids originating from a host, which host is a member of the order of primates.

In another embodiment, the invention includes antibodies generated using the polynucleotide having the sequence shown in SEQ ID NO: 1 or a complementary sequence, fragment or variant thereof or expressed or isolated polypeptides encoded thereby.

In another embodiment, the polynucleotides, polypeptides, or antibody generated therefrom is used to test the effects of modulating IFNω in an *Macaca fascicularis* or other nonhuman primate species of the invention.

BRIEF DESCRIPTION OF THE SEQUENCE LISTING

| SEQ ID NO: | Description |
| --- | --- |
| 1 | Cyno IFNω coding sequence |
| 2 | Cyno IFNω encoded by SEQ ID NO: 1 |
| 3 | Human IFNω protein |
| 4 | Primer |
| 5 | Primer |
| 6 | Primer |
| 7 | Primer |
| 8 | Primer |

DETAILED DESCRIPTION OF THE INVENTION

All publications, including but not limited to patents and patent applications, cited in this specification are herein incorporated by reference as though fully set forth.

Abbreviations

Cyno=Cynomolgus monkey (*Macaca fascicularis*); IFNω=type I human interferon omega; spp.=species; BrdU=5-bromo-2'-deoxyuridine; PBS=phosphate buffered saline; FBS=fetal bovine serum;

Definitions

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region (VH or VL, respectively), a heavy chain or light chain constant region (CH or CL, respectively), a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426, and Huston et al. (1988) Proc. Natl. Acad Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Bird et al. (1988) Science 242:423-426, and Huston et al. (1988) Proc. Natl. Acad Sci. USA 85:5879-5883

As used herein "IFNω" or "IFN omega" refers to an IFNω polypeptide or polynucleotide comprising a coding sequence encoding the IFNω polypeptide. Human IFNω protein sequence is shown in GenBank Acc. No. NP_002168 (SEQ ID NO: 3). The human IFNω protein is 195 amino acids long with a 23 amino acid signal sequence.

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence. Having either a first polynucleotide strand sequence or the antiparallel strand sequence allows immediate recognition of the complementary sequence of one for the other.

The term "polynucleotide" means a molecule comprising a chain of nucleotides covalently linked by a sugar-phosphate backbone or other equivalent covalent chemistry. Double and single stranded DNAs and RNAs are typical examples of polynucleotides. The utility of polynucleotide sequences is their ability to replicate or be replicated in systems using polymerases and be transcribed by ribosomal systems into polypeptides.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "polypeptide" means a molecule that comprises amino acid residues linked by a peptide bond to form a polypeptide. Small polypeptides of less than 50 amino acids may be referred to as "peptides." Polypeptides may also be referred as "proteins."

By "Cynomolgus monkey" or "cyno" is meant *Macaca fascicularis*. The Cynomolgus monkey is also known as the Crab-Eating Macaque, Long-Tailed Macaque, or Java Macaque. The Rhesus monkey (*Macaca mulatto*) is another member of the macaque genus, which belongs to the family known as Old World Monkeys (Cercopithecidae). Cercopithecidae, Hominidae (including humans and great apes), and Hylobatidae (gibbons) make up a suborder or "clade" within the order of primates, called Catarrhini. Macaques live in many different habitats across the globe, making them the most widely distributed genus of nonhuman primates. Macaques (especially *M. mulatta* and *M. fascicularis*) are commonly used in research.

Overview

Due to the absence of cyno IFNω sequence information in the public domain, RNA isolated from cyno airway (trachea) primary epithelial cells was utilized to identify the entire coding sequence of *M. fascicularis* IFNω. It was determined that the protein sequence of *M. fascicularis* IFNω exhibits 93.3% identity and 96.4% similarity to Homo sapiens IFNω. Determination of the cyno IFNω sequence facilitated the recombinant expression, purification, and functional assessment of the protein on human cells expressing an alkaline phosphatase reporter gene under the ISRE promoter. Using this assay, the functional activity of cyno IFNω was found to be comparable to Homo sapiens IFNω and, furthermore, this activity could be reduced by soluble IFNAR2, the high affinity binding chain of the human IFN receptor (Lu, L. LNB 9859, pp110~120, pp 122, pp 126~127, pp 130) as well as with an anti-human IFNω antibody (from PBL). The results describe the nucleic and amino acid sequence of cyno IFNω and demonstrate functional activity of the cyno protein in a human cell based assay thus enabling the potential for characterizing anti-human IFNω mAbs in Cynomolgus monkeys. Therefore, this system will allow the identification of anti-human IFNω lead candidates having functional cross-reactivity to cyno IFNω and hence, enable the use of this non-human primate for pre-clinical studies.

The present invention provides isolated cynomolgus monkey (*Macaca fascicularis*) IFNω polynucleotides, vectors comprising the polynucleotides, isolated host cells, polypeptides obtainable from expression of the polynucleotides, methods for expressing the polypeptides of the invention, and methods of using the polynucleotides and polypeptides of the invention.

Compositions

One aspect of the invention is an isolated polynucleotide comprising a polynucleotide having the sequence shown in SEQ ID NO: 1 or a complementary sequence thereof. The polynucleotide sequence shown in SEQ ID NO: 1 encodes a polypeptide comprising the amino acid sequence as shown in SEQ ID NO: 2, representing the sequence of full length cyno IFNω. In another aspect, the polynucleotide of SEQ ID NO: 1 or a fragment thereof is operably linked to a second polynucleotide sequence for the purpose of e.g., expression in a host cell such as an animal, bacterial cell or an insect cell or creating a fusion protein or a "tagged" protein.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides.

Another embodiment of the invention is a vector comprising an isolated polynucleotide having a sequence shown in SEQ ID NO: 1 or truncated forms as described herein.

The vectors of the invention are useful for maintaining polynucleotides, duplicating polynucleotides, or driving expression of a polypeptide encoded by a vector of the invention in a biological system, including a reconstituted biological system. Vectors may be chromosomal-, episomal- and virus-derived, such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picronaviruses and retroviruses and vectors derived from combinations thereof, such as cosmids and phagemids.

The vectors of the invention can be formulated in microparticles, with adjuvants, with lipid, buffer or other excipients as appropriate for a particular application. In one embodiment of the invention, the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an E. coli origin of replication, an aph (3')-1a kanamycin resistance gene, HCMV immediate early promoter with intron A, a synthetic polyA sequence and a bovine growth hormone terminator. Another exemplary plasmid derived expression vector comprises an E. coli origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide intact glycosylated proteins include Chinese hamster ovary (CHO) cells, HeLa cells, baby hamster kidney cells (BHK, BHK21, ATCC CRL-10), NS0 mouse melanoma cells and derived cell lines, e.g. SP2/0, YB2/0 (ATC CRL-1662) rat myeloma cells, human embryonic kidney cells (HEK, HEK293), human embryonic retina cells PerC.6 cells, hep G2 cells, BSC-1 (e.g., ATCC CRL-26) and many others available from, for example, American Type Culture Collection, Manassas, Va. Populations of cells may comprise an isolated or cultured population of cells or cells present in a matrix such as a tissue.

Mammalian cells such as CHO cells, myeloma cells, BHK cells, mouse Ltk-cells, and NIH3T3 cells have been frequently used for stable expression of heterologous genes. Cell lines such as Cos (COS-1, ATCC CRL 1650; COS-7, ATCC CRL-1651) and HEK293 are routinely used for transient expression of recombinant proteins. A common, preferred bacterial host is E. coli.

Another aspect of the invention is an isolated polypeptide comprising the amino acid sequence as shown in SEQ ID NO: 2, variants, and fragments thereof.

The polypeptides of the invention may comprise fusion polypeptides comprising a polypeptide of the invention fused with second polypeptide. Such second polypeptides may be leader or secretory signal sequences, a pre- or pro- or preproprotein sequence, as well as naturally occurring, or partially synthetic sequences derived in part from a naturally occurring sequence or an entirely synthetic sequence. Secretory signal or leader polypeptide sequences may be selected to direct secretion of the polypeptides of the invention into the lumen of the endoplasmic reticulum or extracellular environment; such polypeptide sequences may be heterologous or endogenous to any polypeptide from a primate species or comprise hybrids of these. Exemplary fusion proteins can be formed by conjugating together a cyno polypeptide having an amino acid sequence shown in SEQ ID NO: 2 and one or more domains derived from or similar to an immunoglobulin domain, such as a CH1, CH2, and CH3 domain. In one aspect, the polypeptide represented by the mature polypeptide (residues 24-195 of SEQ ID NO: 2) is fused to an immunoglobulin Fc domain. Such constructs are well known in the art as described in e.g. U.S. Pat. Nos. 5,116,964, 5,709,859, 6,018,026; WO 04/002417; WO 04/002424; WO 05/081687; and WO 05/032460. One example of such a related construct is a MIMETIBODY™ construct having the generic formula (I):

$$(Bp\text{-}Lk\text{-}(V1)_y\text{-}Hg\text{-}C_H2\text{-}C_H3)_{(t)}, \quad (I)$$

where Bp is a peptide or polypeptide of interest, Lk is a polypeptide or chemical linkage, V1 is a portion of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region, y is 0 or 1, and t is independently an integer of 1 to 10.

Another embodiment of the invention is an antibody that specifically binds a polypeptide of the invention. The polypeptides of the invention can be used to produce polyclonal or monoclonal antibodies against primate IFNω. Techniques for making murine, chimeric, humanized and fully human monoclonal antibodies using protein or nucleic acid immunization are routine and well known to those skilled in the art. Additional discussion and description of such techniques can be found herein below.

Methods of Making the Compositions

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR. Techniques for producing or obtaining polynucleotides of a given known sequence are well known in the art.

Introduction of a polynucleotide, such as a vector, into a host cell can be effected by methods well known to those skilled in the art (Davis et al., Basic Methods in Molecular Biology, $2^{nd}$ ed., Appleton & Lange, Norwalk, Conn., 1994; Sambrook et al., Molecular Cloning: A Laboratory Manual, $3^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lystate based expression systems, wheat germ extract based expression systems, and *E. coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

Another embodiment of the invention is a method for expressing a polypeptide comprising the steps of providing a host cell of the invention; culturing the host cell under conditions sufficient for the expression of a polypeptide comprising the sequence shown in SEQ ID NO: 2 or a variant or fragment thereof; and confirming expression of the polypeptide, variant, or fragment thereof In the methods of the invention, the expression of a polypeptide can be confirmed using a variety of different techniques well known in the art. Detection of the polypeptide of the expected molecular weight using chromatographic techniques or electrophoretic techniques is well known in the art. In order to confirm that the polypeptide comprises the correct primary, secondary, tertiary or higher order structure other techniques must be employed. For example, expression of a polypeptide can be confirmed using detection reagents, such as antibodies or receptor ligands, specific for an expressed polypeptide. Antibodies that specifically bind to or cross-react with the cyno IFNω polypeptides of the invention are one example of such reagents. Detection reagents may be detectably labeled by conjugation or incorporation of a radiolabel, fluorophore, chromophore, an enzyme capable of causing a detectable signal to be produced, or other detectable molecule to, or into, the detection reagent.

Expression of a polypeptide can also be confirmed by assaying for a biological activity associated with IFNω. An exemplary IFNω activity results in induction of antiviral, immunomodulatory, or antiproliferative genes under the interferon-stimulated response element (ISRE), and can be assayed using well known reporter-gene assays or antiviral assays in cells challenged with, for example, murine encephalomyocarditis virus (Adolf et al., J. Biol. Chem. 265:9290-95, 1990)

Methods of Using the Invention

In one embodiment of the invention, the isolated polypeptide of SEQ ID NO: 2 or a fragment thereof is used as an immunogen to elicit or "raise" antibodies in a host such as a rabbit, mouse, rat, guinea pig, or goat. In another embodiment, isolated polypeptide of SEQ ID NO: 2 or a fragment thereof may be used to select molecules capable of binding the polypeptide or fragment thereof from various libraries. It will be recognized that host cells engineered with the polynucleotides of SEQ ID NO: 1 or a fragment thereof or a vector comprising such as polynucleotide may also be used for such purposes. In a particular aspect of the invention the isolated polypeptide of SEQ ID NO: 2 or a fragment thereof is used to select immunoglobulin fragments from a library of such fragments.

In one embodiment of the invention, the polypeptide epitope for binding of an antibody specific for or raised against cyno IFNω determined by a method known in the art such as those described Chapter 11 of Harlow, E. (Ed.), Using antibodies: A Laboratory Manual, 1999. Cold Spring Harbor Laboratory Press, Cold Spring Harbor, N.Y. pp. 379-405. The epitope sequence and/or structure may be compared to other natural homologs or variants or the ability of the antibody to block specific biological functions or binding to receptors can be assessed so that a relationship between the polypeptide sequence or structure at the epitope can be related to the biological functions contributed by the epitope or domain of the IFNω polypeptide.

Another embodiment of the invention is a method of determining cross-reactivity of an IFNω modulator with cyno IFNω. Even if the polypeptides and epitopes are preserved across species and in the species under consideration for a predictive model for a modulator, cross-reactivity of a modulator should be established before additional experimentation is performed (Loisel et al., Crit. Rev. in Onc. Hematol. 62:34-42, 2007). Cross-reactivity of modulators, antibodies of the invention and IFNω antibodies selected based on reactivity to species homolog polypeptides and other antigens may be assayed using, for example, competitive and non-competitive assay systems using techniques, such as BIAcore analysis, FACS, analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art and can be found described in e.g. the Current Protocols series of manuals, published by John Wiley & Sons, Inc., New York and updated regularly. Cross-reactivity can also be evaluated by assaying for inhibition of a biological activity associated with activation of IFNω. Additional discussion of such assays can be found in Harlow (supra).

Another embodiment of the invention is a method for determining if an IFNω modulator is likely to be safe or unsafe for use in humans comprising providing an IFNω modulator, a first *Macaca* spp. monkey (Macaque), and a second *Macaca* spp. monkey; administering the IFNω modulator to the first *Macaca* spp. monkey; and determining whether the first *Macaca* spp. monkey is presenting a deleterious symptom relative to the second monkey, where presentation of a deleterious symptom by the first *Macaca* spp. monkey shows the IFNω modulator is potentially unsafe for use in humans and a lack of presentation of a deleterious symptom by the first *Macaca* spp. monkey shows the IFNω therapeutic is potentially safe in humans.

In the methods of the invention the determination of whether the first *Macaca* spp. monkey is presenting a deleterious symptom relative to the second *Macaca* spp. monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, anemia, infections, paralysis, pain, erythema, dermatitis and the like.

The present invention will now be described with reference to the following specific, non-limiting examples.

EXAMPLE 1

Cloning of CYNO IFNΩ

Determining the Sequence of *Macaca fascicularis* IFNω

Tracheal epithelial cells were obtained after proteolytic digestion of tracheal rings from a normal *Cynomolgus* monkey. Cells were cultured in vitro and a portion was harvested for total RNA. RNA extraction and purification was performed using RNeasy mini spin columns (Qiagen, cat# 74104). The RNA was reverse transcribed using iScript cDNA synthesis kit (BIO-RAD, cat# 170-8891) to obtain a cDNA library.

The full length cyno IFNω was cloned by RT-PCR using primers (5'-ATGTCTTCAGAAAACCTAGGGTCCAA-3', SEQ ID NO:4 and 5'-TGACCAGAGTCACATGTGCAAGT-3', SEQ ID NO:5) designed from 5' and 3' untranslated regions conserved in the human, rhesus, and chimpanzee IFNω sequences (GenBank Acc. Nos: X58822, XM_001108113, XM_528554, respectively) The primers amplified a 718 base pair product, which was gel purified and cloned into a TOPO pCR4 vector (Invitrogen, Carlsbad, Calif.) using standard protocols. Plasmid DNA was purified and sequenced from subsequent transformants The clones contained the full length cyno IFNω coding region. The predicted cyno IFNω protein was 93.3% identical and 96.4% similar to human IFNω, and is shown in SEQ ID NO: 2. A human (SEQ ID NO: 3) versus cyno amino acid sequence alignment is shown in Table 1 (identical residues are highlighted in black, and similar residues are highlighted in grayscale).

CCTCAATGGTGATGGTGATGATGAGATGACCCCA GGTCTC 3', SEQ ID NO:7) that amplified a 629 bp cyno IFNω cDNA. The reaction was run on an agarose gel and the PCR band excised, purified and cloned into Pme I and Nhe I sites in the pBETH vector. Six clones were selected for sequencing (sequencing primer 5' CCACCAGACATAAT-AGCTG 3',SEQ ID NO:8) after subsequent transformation into DH10B cells (Invitrogen, Carlsbad, Calif.) to confirm the correct cyno IFNω sequence.

Expression and Activity of cyno IFNω

To assess activity of cyno IFNω, the protein was expressed in HEK293F cells and purified for subsequent functional studies. Briefly, HEK 293F cells were cultured in a 2L flask at $5 \times 10^5$ cells/mL, 750 mL total and grown for 24 hours. On the day of transfection, 468.75 μg cyno IFNω cDNA in pBETH4 vector was mixed with 468.75 μg pADV vector DNA in 7.5 mL OptiPro® (Invitrogen, Carlsbad, Calif.); in a separate tube, 937.5 μL FreeSyle™ Max Reagent (Invitrogen, Carlsbad, Calif.) was diluted in 7.5 mL OptiPro®. Reagents from the two tubes were mixed and incubated at room temperature for 10 minutes. The mixture was then added directly to HEK293F cells. The cells were grown for 4 more days. The growth media was collected by centrifugation with Sorvall LegendRT bench top centrifuge at $1350 \times g$ for 10 minutes and stored at 4° C.

Cyno IFNω protein was purified from transfection supernatant using Talon Metal Affinity Resin (BD Biosciences Cat#635503) with batch purification method. 2 mL resin slurry (corresponding to 1 mL beads) was washed with $H_2O$ then with PBS. The equilibrated beads were added into transfection supernatant which was filtered with a 0.22 μm filter. The beads-supernatant mixture was rotated at a slow speed for 4 hours at 4° C. The beads were collected and transferred to a 15-mL conical tube. A Pierce Resin Separator (Pierce Cat# 69710) was used to wash the beads, 5 times with 50 mM Sodium Phosphate, 300 mM Sodium Chloride, pH 7.0, and elute the protein with 50 mM Sodium Phosphate, 300 mM Sodium Chloride, 150 mM Imidazole, pH 7.0. The eluted protein was dialyzed into PBS, aliquoted and stored at −80° C. The purified cyno IFNω protein was then run on an SDS-PAGE gel (Invitrogen) using SeeBlue Pre-Stained Standard (Invitrogen) under non-reducing and reducing conditions.

The functional activity of the purified protein was tested in a reporter gene assay using HEK293 cells stably expressing an alkaline phosphatase reporter gene construct driven by

TABLE 1

| Cyno  | 1   | MALLFPLLAALVMTSYSPVGSLGCDLPQNHGLLSRNTLVLLHQMRRISPFLCLKDRRDFR |
| ----- | --- | ----------------------------------------------------------- |
| Human | 1   | MALLFPLLAALVMTSYSPVGSLGCDLPQNHGLLSRNTLVLLHQMRRISPFLCLKDRRDFR |
| Cyno  | 61  | FPQEMVEGSQLQKAQVMSVLHEMLQQIFSLFHTEHSSAAWNTTLLDHLHTGLHRQLEHLE |
| Human | 61  | FPQEMVKGSQLQKAHVMSVLHEMLQQIFSLFHTERSSAAWNMTLLDQLHTGLHQQLQHLE |
| Cyno  | 121 | TCLVQVMREGESAGAIRSPALTLRRYFQGIRVYLKEKKYSDCAWEVVRMEIMKSLFLSTN |
| Human | 121 | TCLLQVVGEGESAGAISSPALTLRRYFQGIRVYLKEKKYSDCAWEVVRMEIMKSLFLSTN |
| Cyno  | 181 | MQERLKSKDGDLGSS |
| Human | 181 | MQERLRSKDRDLGSS |

Subcloning of cyno IFNω cDNA into Expression Vector

Figure 1:
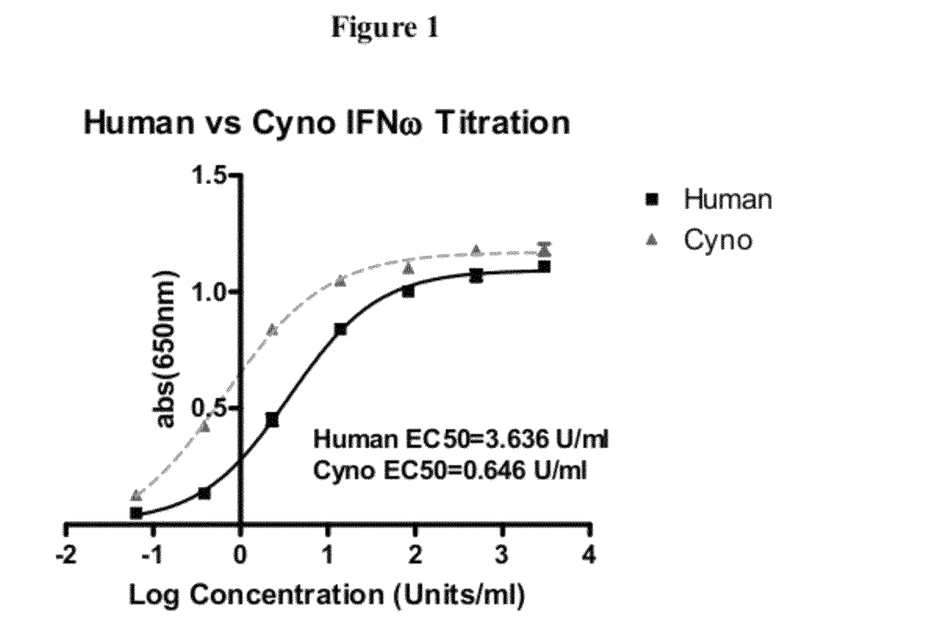
FIG. 1 shows dose-dependent activation of ISRE using both recombinant cyno and human IFNω protein (n=2).

Cyno IFNω cDNA with a C-terminal 6xHis tag was subcloned into pBETH expression vector using primers 5' 3247 mut chimp IFNω (5' GCTGGGTACCAGCTGCTAGCGC-CACCATGGCCCTCCTCTTCCCTCTGC 3', SEQ ID NO:6 and 3' 3260 mut chimp IFNω 5' TCTGTTTAAACGGGCinterferon stimulated response element (ISRE) (Invivogen, Carlsbad, Calif.). Cells were plated in a 96 well flat-bottom, collagen coated plate (Becton Dickinson, cat# 356698) at a concentration of $5 \times 10^4$ cells/well, in 200 μL/well in complete DMEM (Invitrogen, cat# 10569) containing 10% FBS (Invitrogen, cat#16140) and 1% Penicillin/Streptomycin (Invitrogen, cat#15140) and allowed to adhere to plate for 5 hours, after which purified cyno or human IFNω were added to cells at concentrations 0.01 μg/ml (corresponding to approximately 1000 units/ml). The cells were then incubated overnight at 37° C. After ~20 hours, 40 μL of cell supernatant was added to 160 μL of Quanti-Blue™ alkaline phosphatase substrate (Invivogen, cat # rep-qb1), the reaction was allowed to proceed ~6 minutes, and the plates were read with a Spectramax plate reader at 650 nm. The EC50 concentrations for both cyno and human IFNω were calculated using Graphpad Prism 4 software and shown in FIG. 1.

Figure 2:
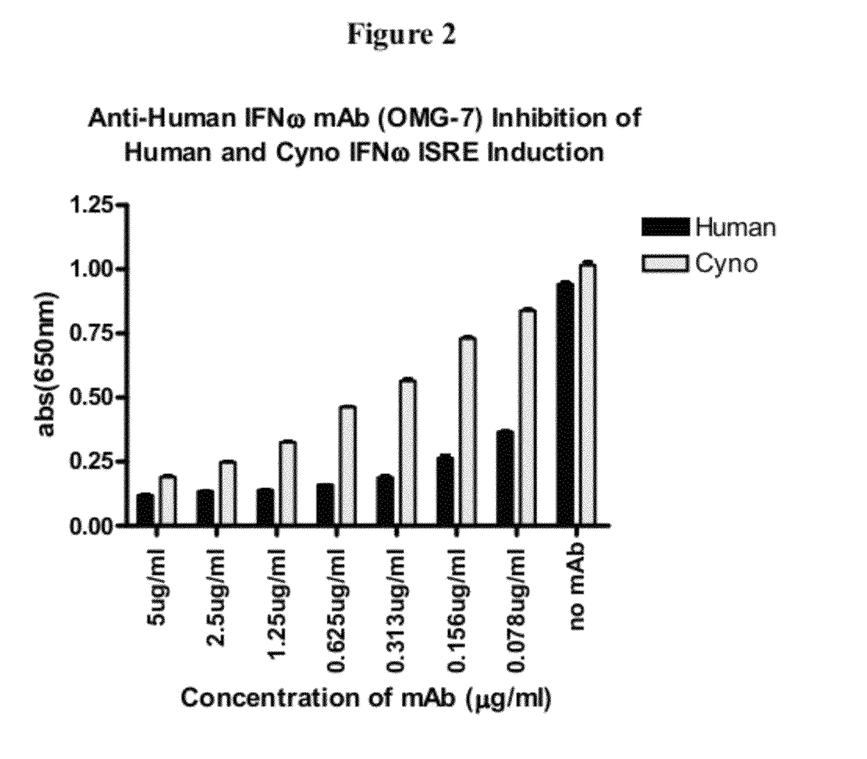
FIG. 2 shows dose-dependent inhibition of cyno and human IFNω-induced ISRE activation by an anti-human IFNω antibody (n=3).
Figure 3:
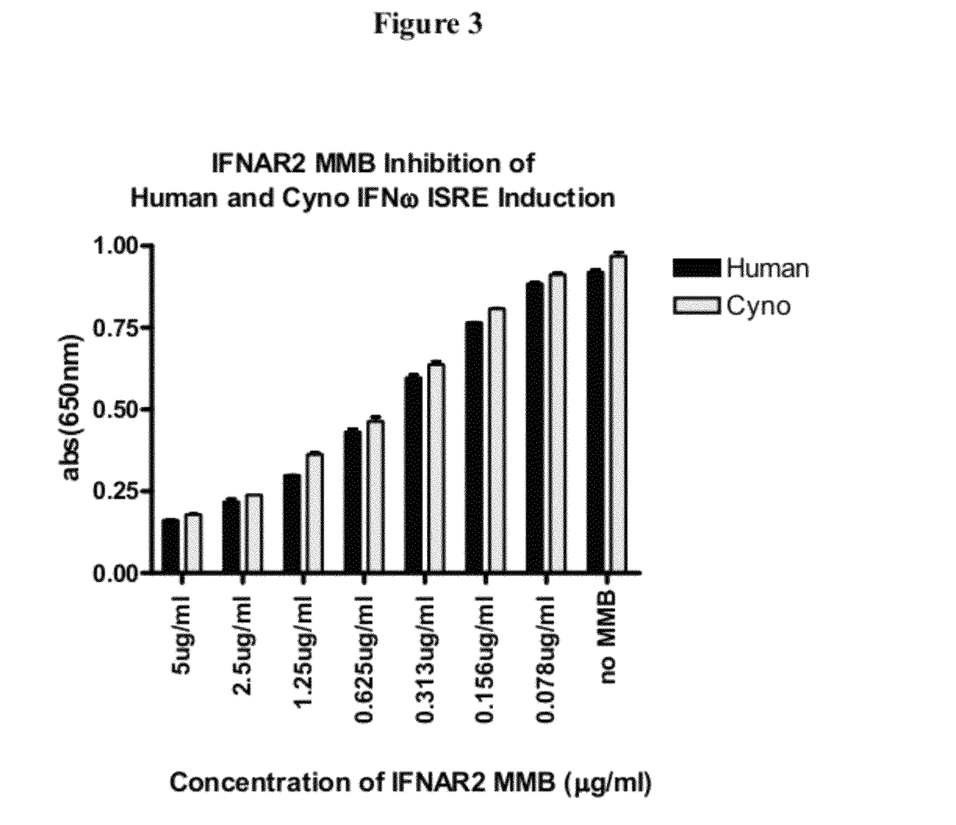
FIG. 3 shows dose-dependent inhibition of cyno and human IFNωinduced ISRE activation by a recombinant, soluble form of the type I interferon alpha receptor-2 (IFNAR2) chain fused to a MIMETIBODY™ scaffold (n=3) (IFNAR2 MMB).

Ability of anti-IFNω antibody OMG-7 (PBL Interferon Source) and a soluble IFNAR2 MMB to block cyno IFNω signaling was assessed using the ISRE reporter gene assay as described above. OMG-7 or soluble IFNAR2 were serial diluted 2-fold, starting at 5 μg/ml down to 0.078 μg/ml followed by addition of cyno or human IFNω EC50s as described above. The cells were incubated with IFN+inhibitor overnight, and the signal detected as above. Both the anti-IFNω antibody (FIG. 2) and the soluble IFNAR2 (FIG. 3) dose-dependently inhibited cyno IFNω activity.

The results indicated that human and cyno IFNω induced similar ISRE activation levels, and thus demonstrated that cyno IFNω was able to bind and signal through the human IFN receptor complex. As the cyno IFNω signaling was inhibited by human soluble IFNAR2 as well as with anti-human IFNω antibody, the cyno IFNω is likely to interact with the human IFN receptor complex in a similar fashion as human IFNω.

What is claimed:

1. An isolated polypeptide comprising a polypeptide having the sequence shown in SEQ ID NO: 2 from residues 24 to 195, wherein the polypeptide is conjugated to an Fc.

2. An isolated polypeptide comprising a polypeptide having the sequence shown in SEQ ID NO: 2, wherein the polypeptide is conjugated to an Fc.

* * * * *